United States Patent
Buchinsky

(10) Patent No.: US 7,567,646 B2
(45) Date of Patent: Jul. 28, 2009

(54) MULTIPLE LAYER DETECTOR FOR SPECTRAL COMPUTED TOMOGRAPHY IMAGING

(75) Inventor: Oded Buchinsky, Raanana (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/088,858

(22) PCT Filed: Sep. 14, 2006

(86) PCT No.: PCT/IB2006/053284

§ 371 (c)(1),
(2), (4) Date: Jul. 14, 2008

(87) PCT Pub. No.: WO2007/039839

PCT Pub. Date: Apr. 12, 2007

(65) Prior Publication Data

US 2008/0315106 A1    Dec. 25, 2008

Related U.S. Application Data

(60) Provisional application No. 60/596,592, filed on Oct. 5, 2005.

(51) Int. Cl.
*A61B 6/00* (2006.01)
(52) U.S. Cl. .................. 378/19; 378/98.8; 250/370.11
(58) Field of Classification Search .............. 378/19, 378/98.8, 98.9; 250/370.08, 370.09, 370.11
See application file for complete search history.

(56) References Cited

U.S. PATENT DOCUMENTS

| 4,647,779 A | 3/1987 | Wong |
| 4,675,526 A | 6/1987 | Rogers et al. |
| 4,677,299 A | 6/1987 | Wong |
| 4,945,241 A | 7/1990 | Yamashita et al. |
| 4,945,243 A | 7/1990 | Arques |
| 5,138,167 A | 8/1992 | Barnes |
| 2003/0173581 A1 | 9/2003 | Blanchard |
| 2004/0022359 A1 | 2/2004 | Acharya et al. |
| 2004/0113085 A1 | 6/2004 | Heismann et al. |
| 2004/0136491 A1 | 7/2004 | Iatrou et al. |
| 2006/0067472 A1* | 3/2006 | Possin et al. ............. 378/98.9 |
| 2006/0102845 A1 | 5/2006 | Williams et al. |

FOREIGN PATENT DOCUMENTS

| DE | 19711927 A1 | 9/1998 |
| DE | 10224227 A1 | 12/2003 |
| EP | 1016881 A2 | 7/2000 |
| WO | 2004095068 A1 | 11/2004 |

OTHER PUBLICATIONS

Deng, et al., Amorphous Silicon Based Solar Cells, Jul. 30, 2002, pp. 1-62.
Hamamatsu, GaAsP photodiode Diffusion type Red sensitivity extended type, 2001, 4 pages, Hamamatsu Photonics K.K., Solid State Division, Hamamatsu City, Japan.
Spectrolab Inc., GaInP2/GaAs/Ge Dual Junction Solar Cells, May 2, 2002, 2 pages, Spectrolab Inc., Sylmar, California, www.spectrolab.com.

* cited by examiner

*Primary Examiner*—Courtney Thomas

(57) ABSTRACT

A radiation detector (100) includes at least first (202) and second (204) scintillators which absorb radiation and generate light at respective first (212) and second (214) wavelengths. The detector also includes at least first (206) and second (208) photodetectors. The first photodetector (206) is substantially non-responsive to light of the wavelength (212) generated by the second scintillator (204). Detectors having three or more scintillators and photodetectors may also be implemented.

24 Claims, 7 Drawing Sheets

MULTIPLE LAYER DETECTOR FOR SPECTRAL COMPUTED TOMOGRAPHY IMAGING

CROSS REFERENCE TO RELATED APPLICATIONS

This application claims the benefit of U.S. provisional application Ser. No. 60/596,592 filed Oct. 5, 2005, which is incorporated herein by reference.

The present invention relates to x-ray detectors for use in spectral computed tomography (CT) systems. It also finds application to the detection of radiation other than x-radiation and in other applications where a radiation detector which discriminates among multiple energies is desired.

Computed tomography (CT) scanners generate images indicative of the x-ray attenuation of an object under examination. The x-ray tubes employed in CT scanners typically produce x-rays having a single, relatively wide energy spectrum. Similarly, the detectors employed in such systems typically provide limited, if any, information about the energy spectrum of the detected radiation. While these scanners provide valuable information about the internal structure of an object under examination, they have limited ability to provide information about the material composition of the object, especially where different compounds have similar radiation attenuations.

The ability to determine the material composition of an object under examination can have various applications. In the medical field, these include the analysis and classification of coronary artery calcification and soft plaque, the analysis and segmentation of neck and head arteries (differentiating between bone and vessel), analyzing and segmenting peripheral artery disease, general enhancement of the contrast between an iodine filled lumen and the vessel wall, quantification in perfusion studies, multi-tissue differentiation and analysis in virtually all body parts, and imaging of small amounts of heavy materials as molecular functional imaging tracers.

Because different compounds can change the attenuated radiation spectrum in different ways, dual-energy scanning has been suggested as a technique for improving material separation capabilities. The idea is to scan with two or more different x-ray spectra or to acquire data using detectors which provide spectral information.

One technique for obtaining data having multiple energy channels or windows is to switch the x-ray tube voltage between multiple values (e.g. 140 kv and 80 kv) in successive frames. Another source-based technique is to provide a radiation filter after the x-ray tube, where the filter is alternated between successive frames. A disadvantage to these techniques is that the number of acquired view is reduced by the number of energy values obtained. Still another technique has been to apply passive filters on the detectors. A disadvantage to this technique is that the spatial resolution has been reduced. Still others have used two detectors, on top of the other. See, e.g., *Technology and Image Results of a Spectral CT System*, B. J. Heismann, et al., SPIE Proceedings Vol. 5368 (May, 2004), pp. 52-59. However, this technique is relatively expensive, limited to a small number of slices, and introduces spectral non-linearity. Photon counting detectors such as CdZnTe or CdTe have also been proposed, although these technologies remain immature and relatively expensive. See, e.g., US Published Patent Application No. 20040022359 entitled Method, System and Computer Product for Plaque Characterization, Acharya, et al.; US Published Patent Application No. 20040136491 entitled Methods and Systems for Detecting Components of Plaque, Iatrou, et al.

Aspects of the present invention address the above matters, and others.

According to one aspect of the present invention, a radiation detector includes a first scintillator which absorbs radiation and produces light at a first wavelength, a second scintillator which absorbs radiation and produces light at a second wavelength, a first photodiode having a first long wavelength cutoff, and a second photodiode having a second long wavelength cutoff. The second wavelength is shorter than the first wavelength. The first photodiode is disposed between the second photodiode and the radiation receiving face and receives light produced by the second scintillator, the second photodiode receives light produced by the first scintillator, and the first long wavelength cutoff is shorter than the second long wavelength cutoff and longer than the second wavelength.

According to a limited aspect of the present invention, the first scintillator is disposed between the second scintillator and the radiation receiving face.

According to another limited aspect of the present invention, the first and second photodiodes are fabricated as a multi-junction device.

According to a more limited aspect of the present invention, the detector includes first and second electrical contacts disposed at a rear of the detector. The first and second electrical contacts are in electrical communication with the first photodiode through vias disposed in the second photodetector.

According to another limited aspect of the present invention, the first scintillator is preferentially responsive to x-radiation having a first energy range and the second scintillator is preferentially responsive to radiation having a second energy range. The first energy range is lower than the second energy range.

According to another limited aspect of the present invention, the detector includes a plurality of radiation detectors disposed a multi-dimensional array.

According to yet another limited aspect of the present invention, the radiation detector includes means operatively connected to the first and second photodiodes for selectively providing a first output signal indicative of radiation absorbed by the first scintillator and a second output signal indicative of radiation absorbed by the first and second scintillators.

According to still another limited aspect of the present invention, the radiation detector includes a third scintillator which absorbs radiation and produces light at a third wavelength and a third photodiode having a third long wavelength cutoff. The third wavelength is shorter than the second wavelength. The third photodiode is disposed between the first photodiode and the radiation receiving face and receives light produced by the third scintillator, and the third long wavelength cutoff is shorter than the first long wavelength cutoff and longer than the third wavelength.

The first scintillator may be disposed between the third scintillator and the radiation receiving face.

According to another aspect of the present invention, a radiation detector includes a first scintillator which absorbs radiation and emits light at a first wavelength, a second scintillator which absorbs radiation and emits light at a second wavelength, a first photodiode which receives light emitted by the second scintillator, and a second photodiode which receives light emitted by the second scintillator and passing through the first scintillator and the first photodiode. The second wavelength is shorter than the first wavelength, the first photodiode has a long wavelength cutoff which is shorter than the first wavelength and longer than the second wavelength, and the second photodiode has a long wavelength cutoff which is longer than the first wavelength.

According to another aspect of the present invention, an apparatus includes a radiation source which emits radiation from a plurality of positions about an examination region and a plurality of detectors. Each detector includes a radiation receiving face which faces the examination region, a first scintillator which preferentially absorbs radiation having a first energy and produces light at a first wavelength, a second scintillator which preferentially absorbs radiation having a second energy and produces light at a second wavelength, a first photodetector having a first long wavelength cutoff, and a second photodetector having a second long wavelength cutoff. The first photodetector is disposed between the second photodetector and the radiation receiving face, the second scintillator is disposed between the first photodetector and the radiation receiving face, the first scintillator is disposed between the second scintillator and the radiation receiving face, and the first long wavelength cutoff is shorter than the second long wavelength cutoff.

Still other aspects of the present invention will be understood by those skilled in the art upon reading and understanding the appended description.

Figure 1:
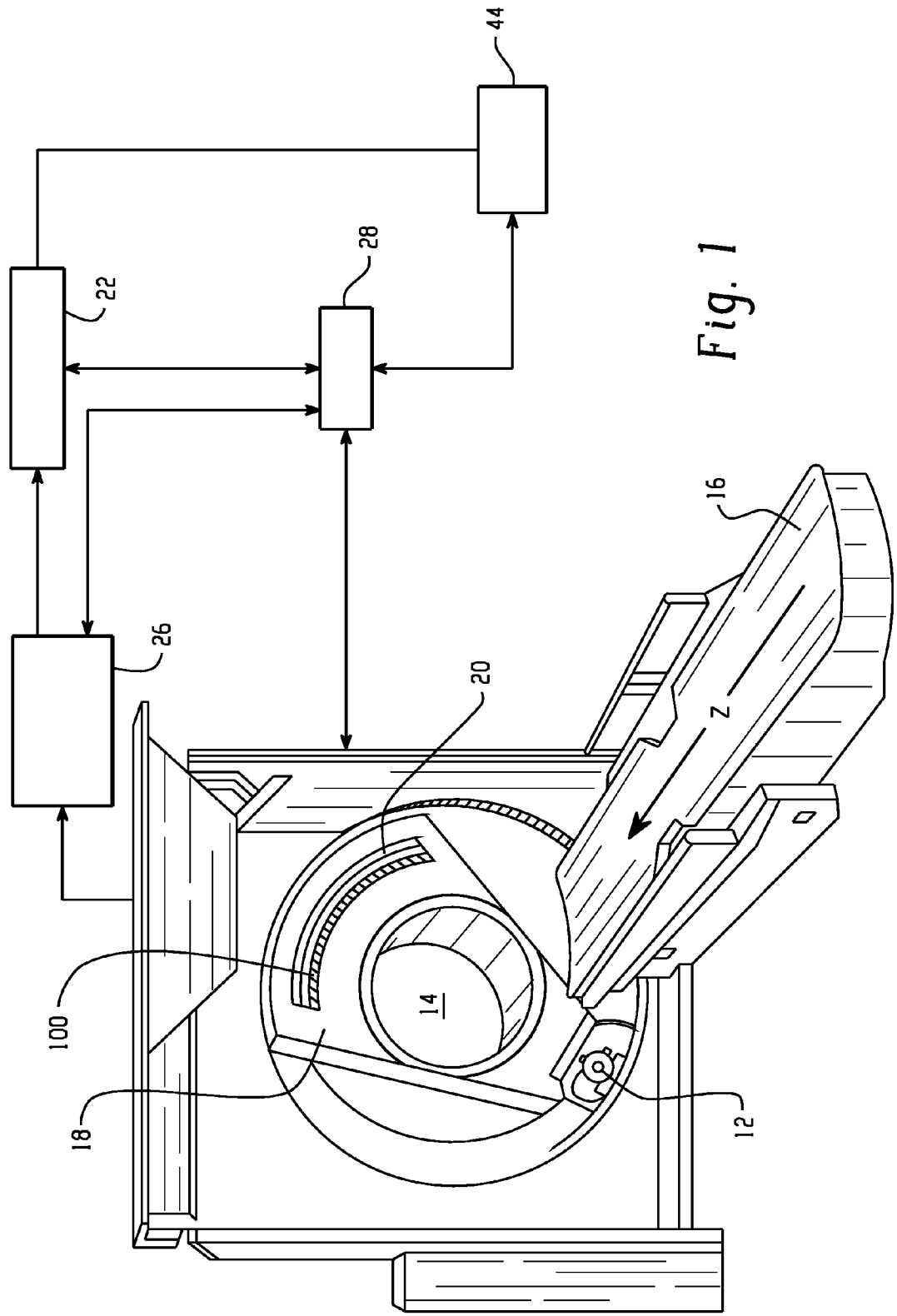
FIG. 1 depicts a CT scanner.

With reference to FIG. 1, a computed tomography (CT) scanner includes a rotating gantry 18 which rotates about an examination region 14. The gantry 18 supports an x-ray source 12 such as an x-ray tube. The gantry 18 also supports an x-ray sensitive detector 20 which subtends an angular arc on the opposite side of the examination region 14. X-rays produced by the x-ray source 12 traverse the examination region 14 and are detected by the detector 20. Accordingly, the scanner 10 generates scan data indicative of the radiation attenuation along a plurality of projections or rays through an object disposed in the examination region 14.

A support 16 such as a couch supports a patient or other object in the examination region 14. The patient support 16 is preferably movable in the z-direction. In a helical scan, movement of the support 16 and the gantry 18 are coordinated along with such that the x-ray source 12 and the detectors 20 traverse a generally helical path with respect to the patient.

The detector 20 includes a plurality of detector elements 100 disposed in an arc which extends in the transverse direction. The detector elements 100 each produce signals indicative of radiation detected at two or more energies or energy ranges. In the case of a multi-slice or area detector, the detector elements 100 are arranged in a two dimensional array also extending in the z-direction. As an aid to fabrication, a plurality of smaller or sub-arrays of detector elements are in turn assembled to form the larger detector 20.

Depending on the configuration of the scanner 10 and the detectors 20, the x-ray source 12 generates a generally fan, wedge, or cone shaped radiation beam. Moreover, a so-called fourth generation scanner configuration, in which the detector 20 spans an arc of 360 degrees and remains stationary while the x-ray source 12 rotates, may also be implemented, as may detectors arranged in flat panel array.

A data measurement system 26 located near the detector 20 contains signal processing circuitry which amplifies and digitizes the output signals produced by the various detector elements and energy ranges. Data generated by the data measurement system 26 is reconstructed to generate volumetric data indicative of the interior anatomy of the patient. More particularly, the data from the various energy ranges is processed to provide information about the material composition of the object under examination.

A controller 28 coordinates the various scan parameters as necessary to carry out a desired scan protocol, including x-ray source 12 parameters, movement of the patient couch 16, and operation of the data measurement system 26.

A general purpose computer serves an operator console 44. The console 44 includes a human readable output device such as a monitor or display and an input device such as a keyboard and mouse. Software resident on the console allows the operator to control the operation of the scanner by establishing desired scan protocols, initiating and terminating scans, viewing and otherwise manipulating the volumetric image data, and otherwise interacting with the scanner.

Figure 2A:
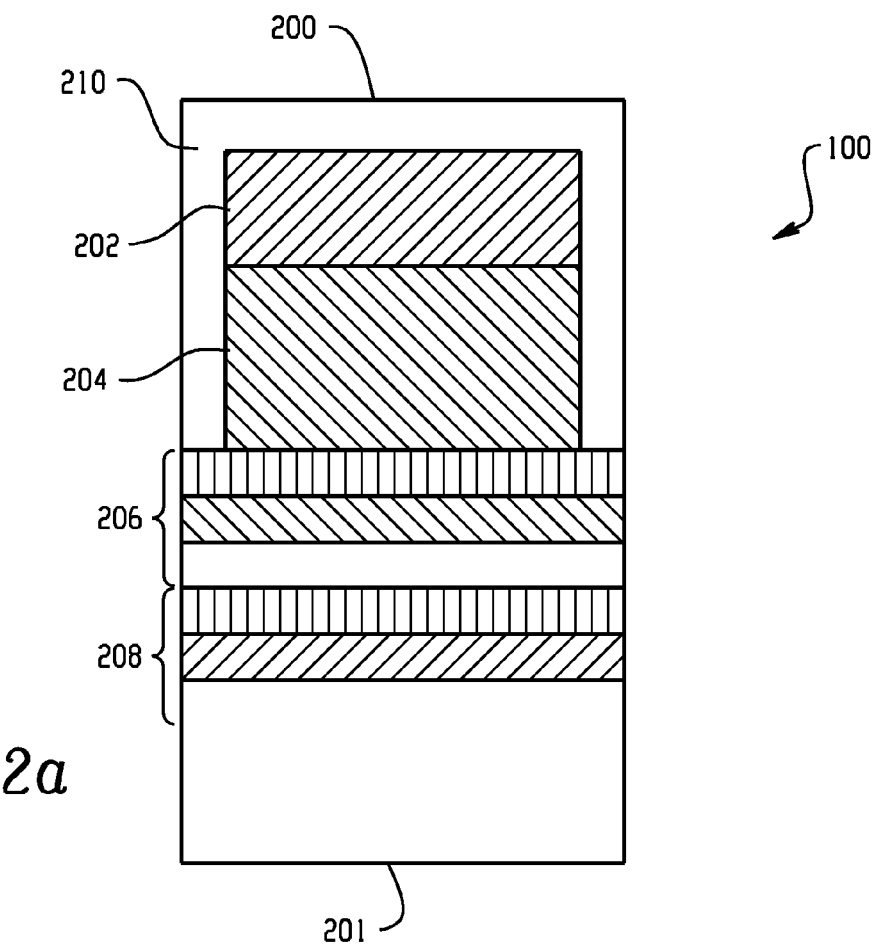
FIG. 2a depicts a first radiation detector.

Turning now to FIG. 2a, the detector elements 100 include a front or radiation receiving face 200 which faces the examination region 14 and receives radiation generated by the x-ray source 12. Positioned in sequence toward the bottom or rear 201 of the detector element 100 is a first scintillator 202, a second scintillator 204, a first photodetector 206, and a second photodetector 208. The front face of the first scintillator 202 and the four (4) sides of the first and second scintillators 202, 204 are surrounded by a light reflector 210 such as a layer containing a titanium dioxide ($TiO_2$) based material.

Figure 2B:
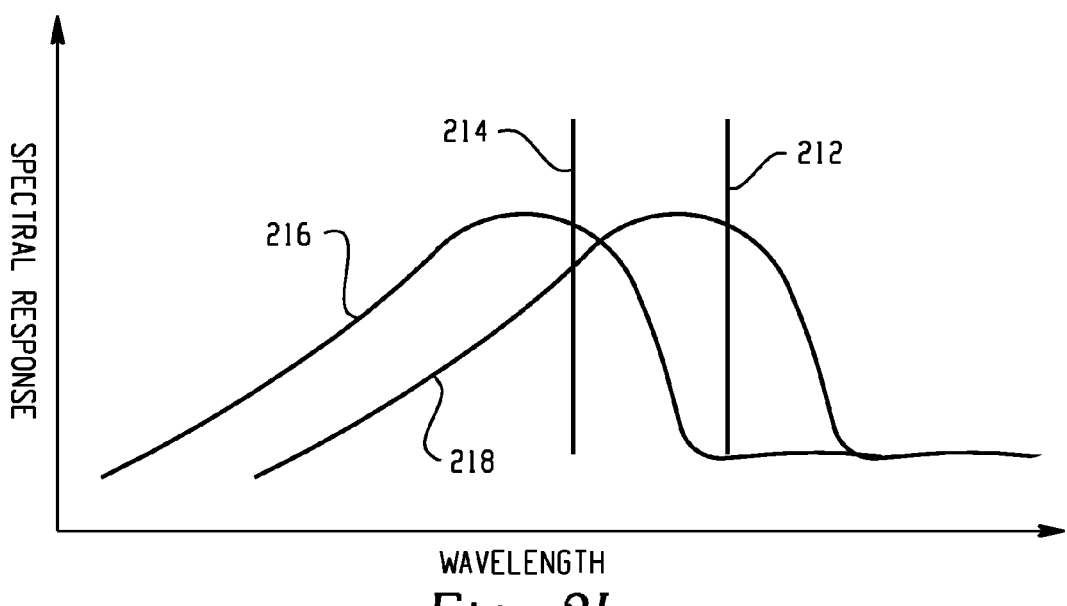
FIG. 2b depicts spectral characteristics of the first radiation detector.

FIG. 2b depicts the spectral characteristics the scintillators 202, 204 and photodetectors 206, 208. The materials and relative thicknesses of the first 202 and second 204 layers are preferably selected so that the first layer preferentially absorbs radiation having a relatively longer wavelength (or stated conversely, a lower energy), whereas the second layer preferentially absorbs radiation having a relatively shorter wavelength (or stated conversely, a higher energy). In one embodiment, the first scintillator 202 is a relatively low-Z material, while the second scintillator 204 is a relatively denser, high-Z material. The thickness of the scintillators 202, 204 is optimized according the x-ray energies to be absorbed in each layer.

The first scintillator 202 emits light having an emission spectrum generally centered at a first relatively longer wavelength 212; the second scintillator 204 emits light generally centered at a second relatively shorter wavelength 214.

In an embodiment particularly well suited for computed tomography imaging, the first scintillator 206 is fabricated from tellurium-doped zinc selenide (ZnSe:Te) which emits light centered at approximately 635 nm, and the second scintillator 208 is fabricated from gadolinium oxysulfide ($Gd_2O_2S$ or GOS) which emits light centered at approximately 510 nm. Various other scintillator combinations may be implemented.

With continuing reference to FIG. 2b, the spectral response (i.e., the output of the photodetector as a function of photon wavelength) of the first photodetector 206 is depicted at 216.

The first photodetector 206 is responsive to light of a wavelength generated by the second scintillator 204 and substantially non-responsive to light of the wavelength 212 generated by the first scintillator 202. The spectral response of the second photodetector 206 is depicted at 218. The first photodetector 206 is responsive to light of a wavelength generated by the first scintillator 202.

Figure 2C:
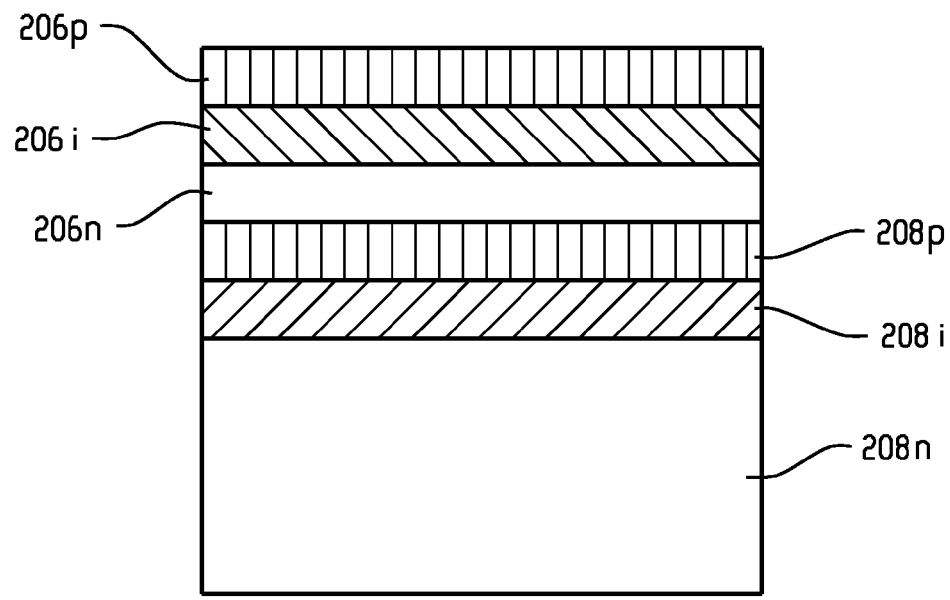
FIG. 2c depicts a photodetector layers of the first radiation detector.

Turning now to FIG. 2c, the first photodetector 206 is preferably a PIN photodiode which includes a p-layer 206p, an interstitial layer 206i, and an n-layer 206n. Likewise, the second photodetector 208 is preferably a PIN photodiode which includes a p-layer 208p, an interstitial layer 208i, and an n-type substrate (GaP, for example) 208n. The photodiodes 206, 208 are preferably fabricated or grown as a single structure to form a single multi-junction device.

The band gap energy is the minimum energy required for a photon to excite an electron from the valence band to the conduction band and is equal to energy gap between the maxima of the valance and the minima of the conduction band. The wavelength associated with this energy is the maximum wavelength of an effective photon, and is known as the long wavelength cutoff of the photodiode:

$$\lambda = \frac{hc}{E} \quad \text{Equation 1}$$

where $\lambda$ is the long wavelength cutoff, h is Planck's constant, c is the speed of light, and E is the band gap energy. The photodiode becomes substantially non-responsive to incident photons have a wavelength greater than the long wavelength cutoff.

Photodiode band gaps can be engineered to tailor photodiode spectral response within a relatively wide range. The spectral response of gallium arsenide (GaP) and gallium arsenide phosphide (GaAsP) photodiodes, for example, can be tailored to cover the visible light range. More particularly, the composition and thickness of the respective interstitial layers 206i, 208i are selected to provide the desired band gap.

Figure 2D:
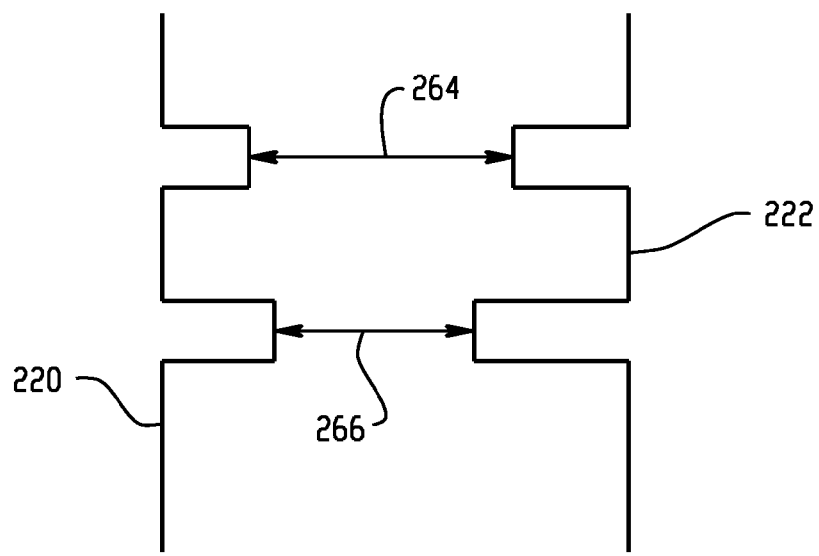
FIG. 2d depicts band gaps of the first radiation detector.

FIG. 2d is a schematic depiction of the energy band gap between the valence 220 and conduction 222 bands of the photodiodes 206, 208. The band gap 264 of the absorption layer of the first photodiode 206 is wider than the band gap 266 of the absorption layer of the second photodiode 208 such that the first photodiode 206 preferentially responsive to light having a relatively higher energy (or stated conversely, a shorter wavelength) than the second photodiode 208. Moreover, the band gap 264 of the first photodiode 206 is selected so that its long wavelength cutoff is shorter than the wavelength 212 of the light emitted by the first scintillator 202 and longer than the wavelength 214 of the light emitted by the second scintillator 204. When arranged such a configuration, the first photodiode is relatively transmissive of light of a wavelength 212 emitted by the first scintillator 204, and each photodiode 206, 208 is substantially responsive to light generated by a single scintillator.

In this regard, it should be noted that the spectral responses 216, 218 of the first and second photodiodes 202, 204 may overlap over a range of energies, as long as they are shifted. The upper or front most photodetectors are relatively transmissive of light absorbed by the lower or rearmost photodetectors.

The first and second photodiodes 206, 208 are preferably fabricated from gallium arsenide (GaP), gallium arsenide phosphide (GaAsP) or indium phosphide (InP) based technologies. PN junctions on other suitable layer structures are also contemplated. Other technologies or photodetectors which can be tailored to have the desired spectral response may also be implemented.

Table 1 depicts suitable scintillator emission spectra and photodiode response for a detector 100 where the first scintillator 202 comprises ZnSe:Te and the second scintillator is comprises GOS. Of course, those skilled in the art will recognize that these parameters are exemplary only and will vary based on the material characteristics and structure of a particular implementation. Other combinations can also be valid.

TABLE 1

| | Center of Emission Spectrum (nm) | Photodiode Band Gap (ev) | Photodiode Long Wavelength Cutoff (nm) |
|---|---|---|---|
| First Scintillator 202 | 635 | | |
| Second Scintillator 204 | 510 | | |
| First Photodetector 206 | | 2.3 | 540 |
| Second Photodetector 208 | | 1.55 | 800 |

Figure 3A:
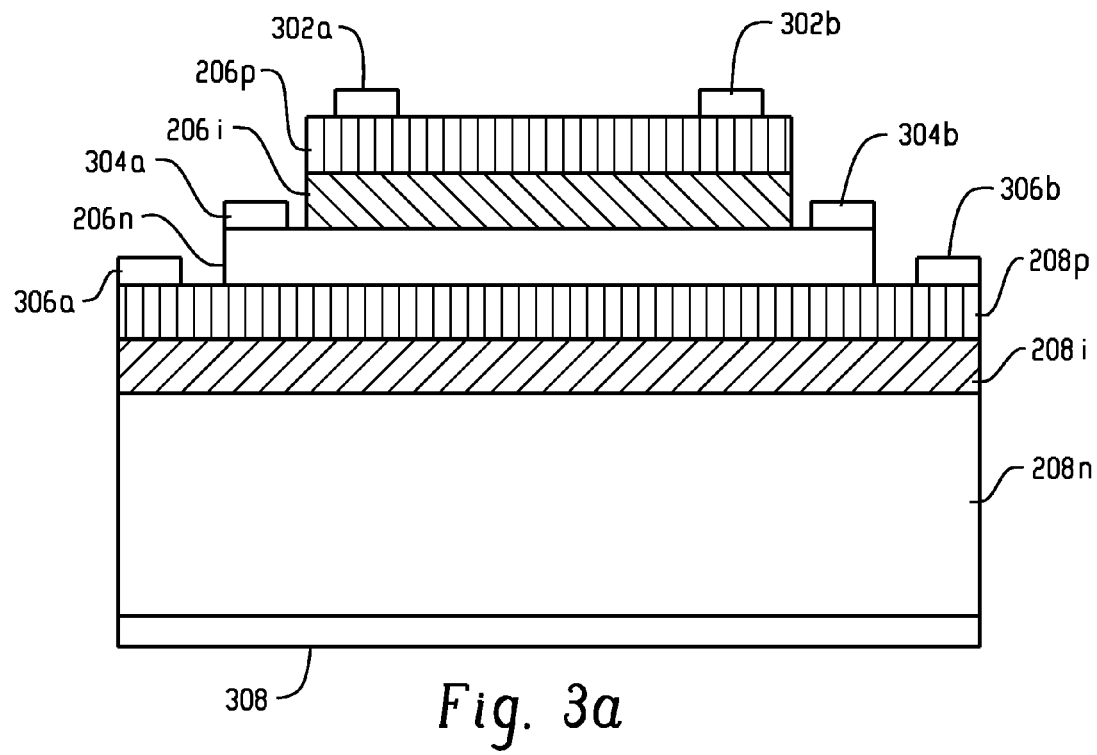
FIGS. 3a and 3b depict electrical connections for the first radiation detector.

Electrical contacts provide an electrical contact with each photodiode 206, 208. FIG. 3a depicts a first connection arrangement for a multi-junction photodiode structure. In one embodiment, one or more electrical contacts 302a, 302b provide an electrical connection with the first p-layer 206p while one or more contacts 304a, 304b provide electrical contact with the first n-layer 206n. One or more electrical contacts 306a, 306b provide an electrical connection with the second p-layer 208p while one or more contacts such as contact 308 provide electrical contact with the second n-layer 208n. Accordingly, the respective contacts receive output signals from each photodiode.

Figure 3B:
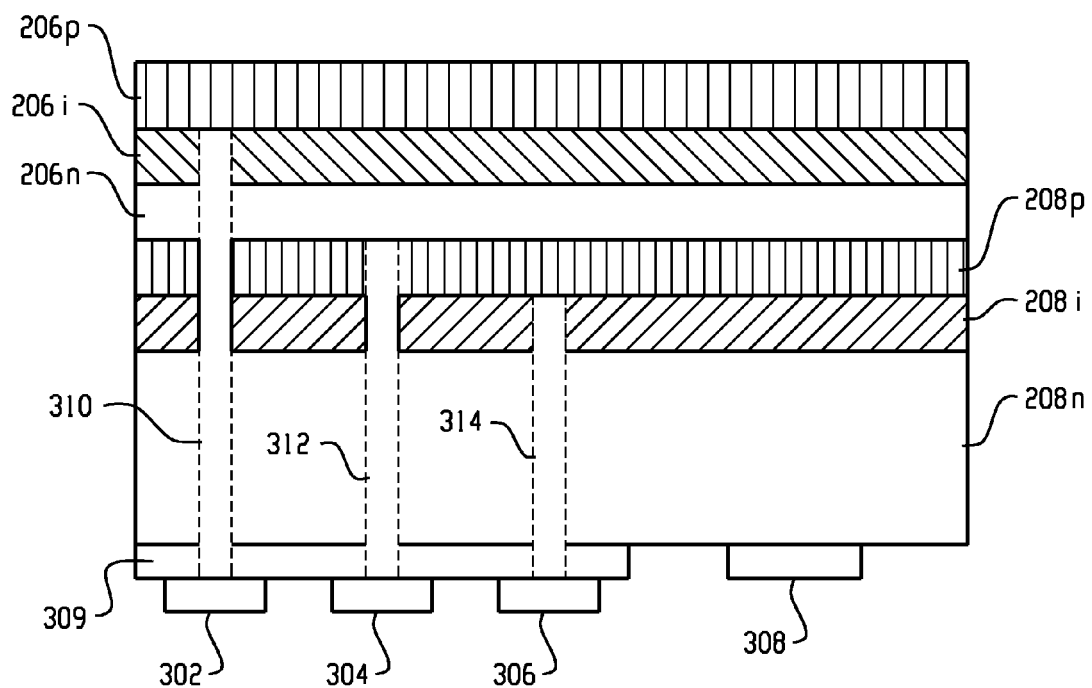

FIG. 3b depicts a second connection arrangement where the electrical contacts 302, 304, 306, 308 are disposed to the rear of the photodiode structure. An insulating layer 309 insulated the contacts 302, 304, 306 from the rear-most n-layer 208n. Electrical connections to the corresponding diode layers 206p, 206n, 208p, are provided by way of corresponding vias or through holes 310, 312, 314. The second arrangement facilitates the fabrication of tiled back illuminated detector arrays in which individual detector elements 100 or groups of detector elements 100 are arranged in a multi-dimensional array. Such arrays find particular application in computed tomography and other radiation detection applications where relatively larger arrays of detector elements 100 are desired.

Of course, other suitable connection arrangements may also be implemented.

Figure 5:
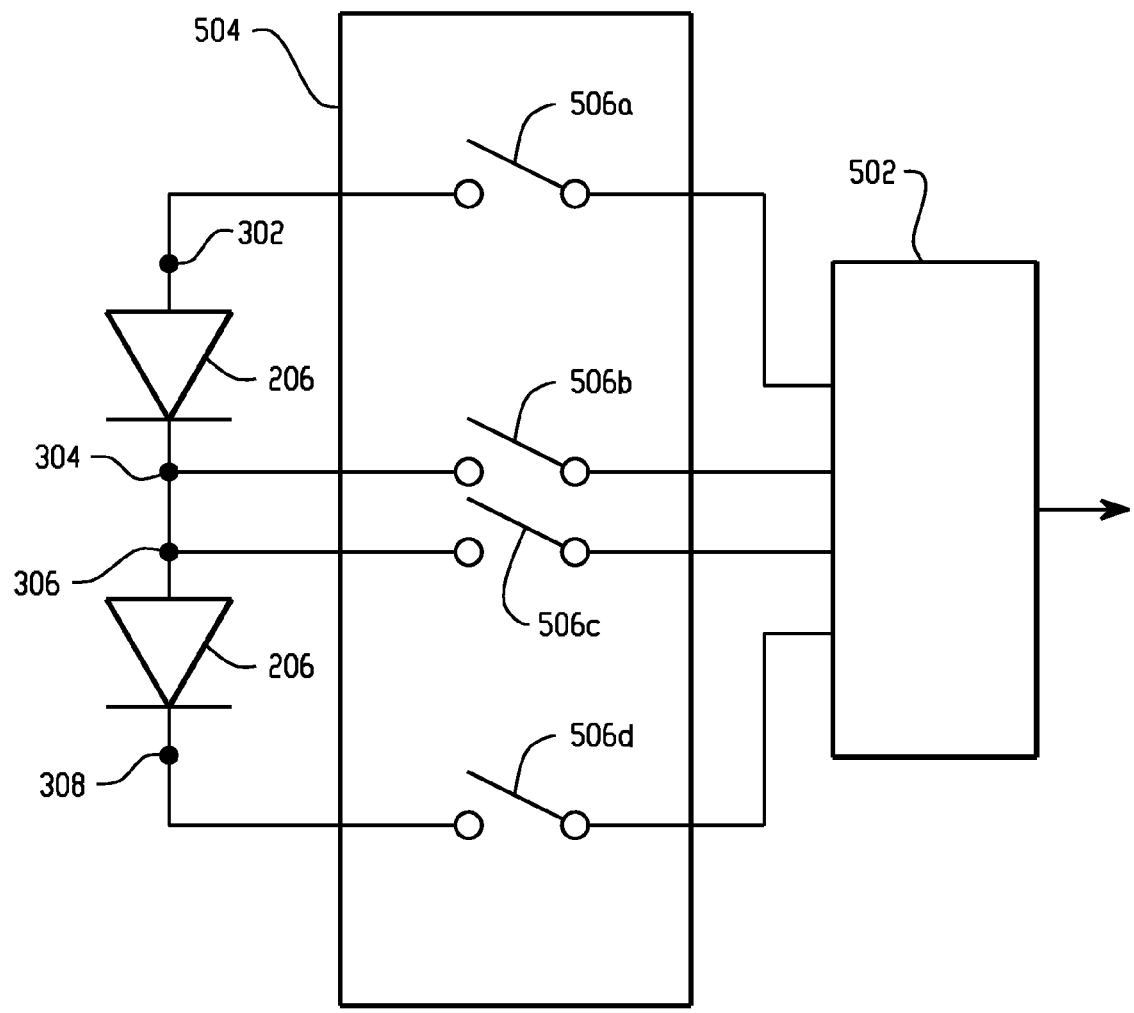
FIG. 5 depicts an exemplary multiplexing arrangement for a dual energy detector.

FIG. 5 depicts an exemplary multiplexing arrangement for a dual energy detector such as the one described above in relation to FIG. 2. The contacts 302, 304, 306, 308 for the photodetectors 206, 208 are electrically connected to suitable signal amplification and processing circuitry 502 by way of a multiplexer 504. By suitably controlling the various switches in the multiplexer 504, the amplifier 502 selectively generates an output indicative of the signal from by first photodiode 206 and hence the first energy, the signal generated by the second photodiode 208 and hence the second energy, or the combined signals from the first 206 and second 208 photodiodes and hence the combined first and second energies. Various multiplexer configurations and the resulting outputs are depicted in Table 3.

TABLE 3

| Switch 506a | Switch 506b | Switch 506c | Switch 506d | Amplifier 504 Output |
|---|---|---|---|---|
| Closed | Closed | Open | Open | First Energy |
| Open | Open | Closed | Closed | Second Energy |
| Closed | Closed | Closed | Closed | Separate signals of both first and second energies |
| Closed | Open | Open | Closed | Combined First and Second Energies |

It may also be desirable to multiplex the amplifier 502 among more than one detector element 100, especially in systems having a relatively large number of detector elements 100. Depending on the configuration of the amplifier 502, different connection schemes may also be implemented.

Figure 4A:
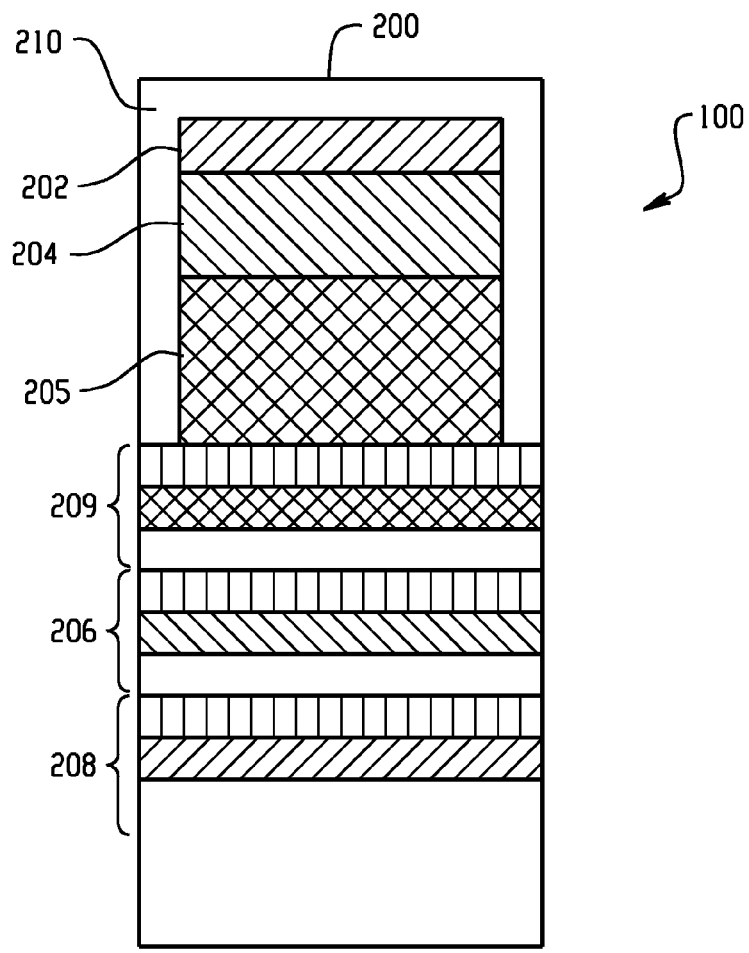
FIG. 4a depicts a second radiation detector.
Figure 4B:
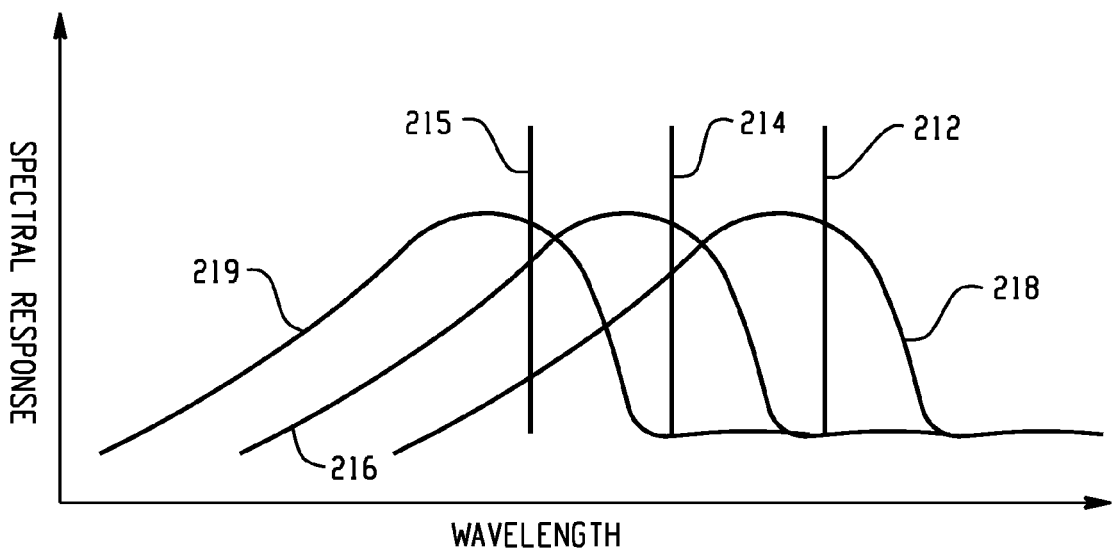
FIG. 4b depicts spectral characteristics of the second radiation detector.

While the above discussion has focused on a dual energy detector element 100, detector elements providing outputs indicative of three or more energies or energy spectra may also be implemented. FIG. 4a depicts a detector element having a third scintillator 205 and third photodetector 209. FIG. 4b depicts the spectral response of the scintillators 202, 204, 205 and photodetectors 206, 208, 209. The third scintillator 205 emits light generally centered at a third relatively shorter wavelength 215. The third photodetector 209 likewise responds to light having a third relatively shorter wavelength 219.

Figure 4C:
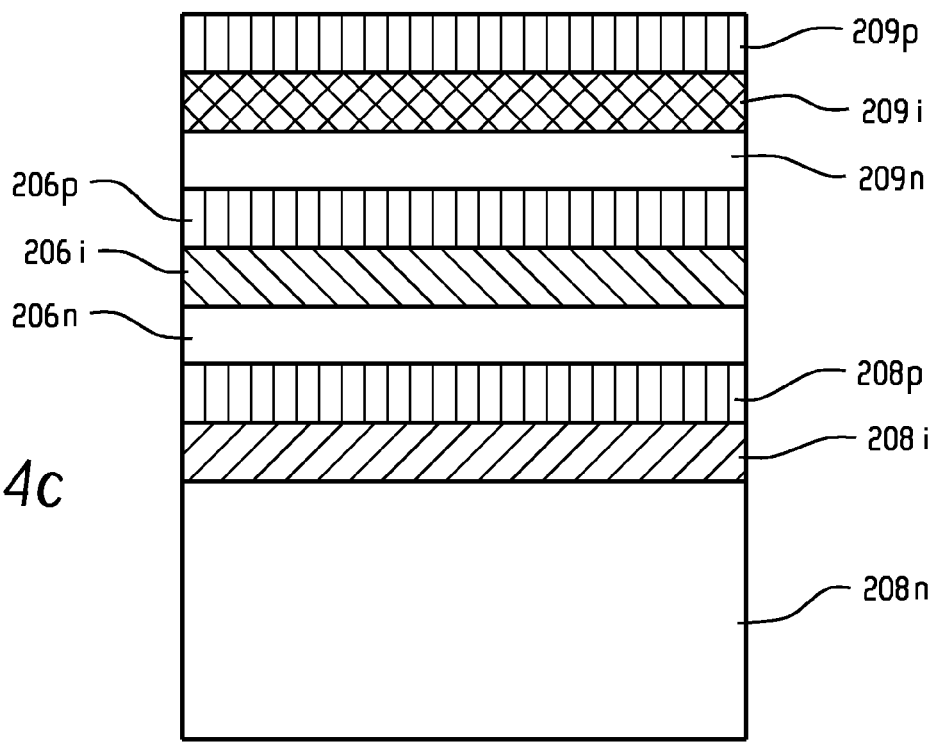
FIG. 4c depicts photodetector layers of the second radiation detector.
Figure 4D:
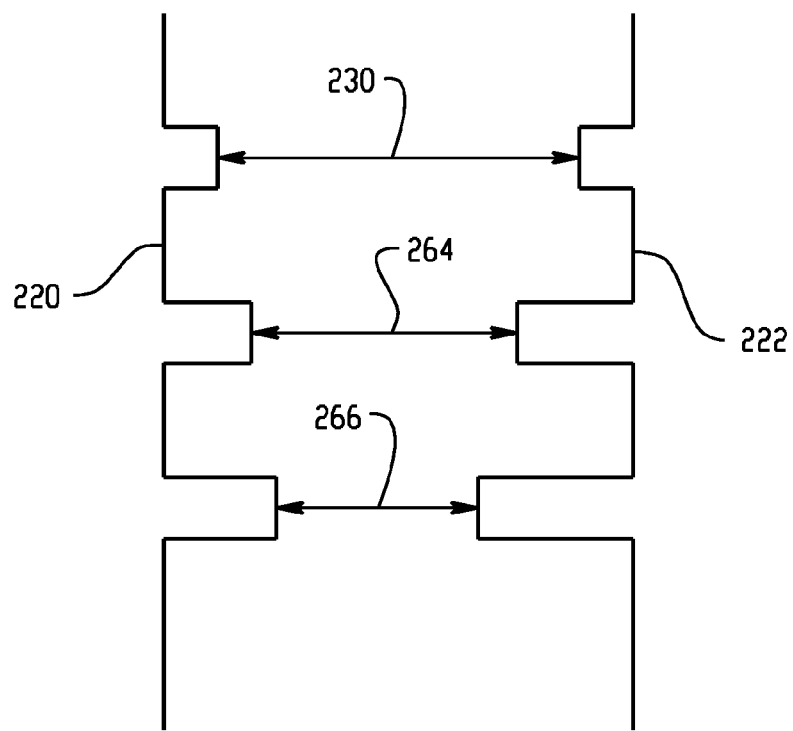
FIG. 4d depicts band gaps of the second radiation detector.

The photodiode layer structure and corresponding band gaps are illustrated in FIGS. 4c and 4d respectively. The third photodetector 209 is likewise a PIN photodiode which includes a p-layer 208p, an interstitial layer 208i, and an n-type substrate (GaP for instance) 208n. The photodiodes 206, 208, 209 are preferably fabricated or grown so that that the photodiodes 206, 208, 209 form a single multi-junction device. Other layer structures (such as PN, etc.) can also be implemented, provided that the desired spectral response is achieved.

The band gap 230 of the third photodiode 209 is wider than the band gap 264 of the first photodiode 206 such that the first photodiode 206 is preferentially responsive to light having a relatively lower energy (or stated conversely, a longer wavelength) than the third photodiode 209. Moreover, the band gap 230 of the third photodiode 209 is selected so that its cutoff wavelength is shorter than the wavelength 214 of the light emitted by the second scintillator 204 and longer than the wavelength 215 of the light emitted by the third scintillator 205.

In an embodiment particularly well suited for computed tomography imaging, the first scintillator 206 is fabricated from tellurium-doped zinc selenide (ZnSe:Te) which emits light centered at approximately 635 nm, the second scintillator 208 is fabricated from gadolinium oxysulfide ($Gd_2O_2S$ or GOS) which emits light centered at approximately 510 nm, and the third scintillator is fabricated from LySO, which emits light centered at approximately 420 nm. Various other scintillator combinations may be implemented.

Table 2 depicts suitable scintillator emission spectra and photodiode response for such a detector 100. Of course, those skilled in the art will recognize that these parameters are exemplary only and will vary based on the material characteristics and structure of a particular implementation. Other combination can also be valid.

TABLE 2

|  | Center of Emission Spectrum (nm) | Photodiode Band Gap (ev) | Photodiode Long Wavelength Cutoff (nm) |
|---|---|---|---|
| First Scintillator 202 | 635 | | |
| Second Scintillator 204 | 510 | | |
| Third Scintillator 205 | 420 | | |
| Third Photodetector 209 | | 2.7 | 460 |
| First Photodetector 206 | | 2.3 | 540 |
| Second Photodetector 208 | | 1.55 | 800 |

Electrical connections are made in a manner analogous to those described above in relation to FIG. 3. The multiplexing and signal processing arrangement described above in connection with FIG. 5 can likewise be readily extended to detectors 100 providing signals indicative of three or more energies.

In operation, the x-ray source 12 rotates about the examination region 14 to emit x-rays from a plurality of locations thereabout. The x-rays emitted by the source 12 are attenuated by an object disposed in the examination region 14, and are received by radiation sensitive faces 200 of the respective detector elements 100.

In the three energy arrangement described in connection with FIG. 4, radiation having the third, relatively highest energy is preferentially absorbed the third scintillator 205 after passing through the first 202 and second 204 scintillators. The third scintillator 205 generates light having the third, relatively shortest wavelength 215. As the third photodiode 209 is responsive to light having the third wavelength 215 but not the first 212 and second 214 wavelengths, the output signal generated by the third photodiode 209 is indicative of the light generated by the third scintillator 205.

Radiation having the second, intermediate energy is preferentially absorbed by the second scintillator 204 after passing through the first 202 scintillator. The second scintillator 204 generates light having an intermediate wavelength 214. Light emitted by the second scintillator 204 which passes through the third scintillator 205 and the third photodiode 209 is largely absorbed by the second photodetector 206, which generates an output signal indicative of the second energy range.

Radiation having the first, relatively highest energy is preferentially absorbed the third scintillator 205, which generates light having the first, relatively longest wavelength 212. Light emitted by the first scintillator 202 which passes through the third and first photodetectors 209, 206 is largely absorbed by the second photodetector 208, which generates an output signal indicative of the first energy range.

The signals generated by the respective photodiodes 206, 208, 209 are selectively multiplexed so as to generate output signals of the respective energy ranges, as well as the different combinations of energy ranges. These output signals are processed and reconstructed to generate volumetric data indicative of the radiation attenuation of the object at one or more of the desired energy ranges and/or the material composition of the object as required by the needs of a particular application.

While the above operational description has focused on a detector element 100 which discriminates among three energies, the dual energy detector element 100 operates similarly, but with the third scintillator 205 and the third photodetector 209 omitted. The detector structure and operation may likewise be extended to detector elements 100 which discriminate among four or more energies.

The detector elements 100 are applicable to applications other than CT scanners where the ability to discriminate among radiation having various energy ranges is desired. Moreover, by selecting suitable scintillators and appropriately tailoring the photodetector response, the detectors suitable to gamma and radiation having other energies may also be produced.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

What is claimed is:

1. A radiation detector having a radiation receiving face, the radiation detector comprising:
   a first scintillator which absorbs radiation and produces light at a first wavelength;
   a second scintillator which absorbs radiation and produces light at a second wavelength, wherein the second wavelength is shorter than the first wavelength;
   a first photodiode having a first long wavelength cutoff;
   a second photodiode having a second long wavelength cutoff, wherein the first photodiode is disposed between the second photodiode and the radiation receiving face and receives light produced by the second scintillator, wherein the second photodiode receives light produced by the first scintillator, and wherein the first long wavelength cutoff is shorter than the second long wavelength cutoff and longer than the second wavelength;
   a first electrical contact; and
   a second electrical contact, wherein the first and second electrical contacts are in electrical communication with the first photodiode through vias disposed in the second photodiode.

2. The radiation detector of claim 1 wherein first scintillator is disposed between the second scintillator and the radiation receiving face.

3. The radiation detector of claim 1 wherein the first and second photodiodes are fabricated as a multi-junction device.

4. The radiation detector of claim 3 including the first and second electrical contacts being disposed at a rear of the detector.

5. The radiation detector of claim 1 wherein the first scintillator is preferentially responsive to x-radiation having a first energy range and the second scintillator is preferentially responsive to radiation having a second energy range, and wherein the first energy range is lower than the second energy range.

6. The radiation detector of claim 1 including plurality of radiation detectors disposed a multi-dimensional array.

7. The radiation detector of claim 1 including means operatively connected to the first and second photodiodes for selectively providing a first output signal indicative of radiation absorbed by the first scintillator and a second output signal indicative of radiation absorbed by the first and second scintillators.

8. The radiation detector of claim 1 including
   a third scintillator which absorbs radiation and produces light at a third wavelength, wherein the third wavelength is shorter than the second wavelength;
   a third photodiode having a third long wavelength cutoff, wherein the third photodiode is disposed between the first photodiode and the radiation receiving face and receives light produced by the third scintillator, and wherein the third long wavelength cutoff is shorter than the first long wavelength cutoff and longer than the third wavelength.

9. The detector of claim 8 wherein the first scintillator is disposed between the third scintillator and the radiation receiving face.

10. A radiation detector comprising:
    a first scintillator which absorbs radiation and emits light at a first wavelength;
    a second scintillator which absorbs radiation and emits light at a second wavelength, the second wavelength being shorter than the first wavelength;
    a first photodiode which receives light emitted by the second scintillator, wherein the first photodiode has a long wavelength cutoff which is shorter than the first wavelength and longer than the second wavelength;
    a second photodiode which receives light emitted by the second scintillator and passing through the second scintillator and the first photodiode, wherein the second photodiode has a long wavelength cutoff which is longer than the first wavelength;
    first electrical contact; and
    a second electrical contact, wherein the first and second electrical contacts are in electrical communication with the first photodiode through vias disposed in the second photodiode.

11. The radiation detector of claim 10 wherein the radiation detector includes a radiation receiving face and the first scintillator is disposed between the second scintillator and the radiation receiving face.

12. The radiation detector of claim 11 wherein the first photodiode is disposed between the second photodiode and the radiation receiving face.

13. The radiation detector of claim 12 including the first and second electrical contacts disposed at a rear of the radiation detector.

14. The radiation detector of claim 10 wherein the first scintillator is preferentially responsive to x-radiation having a first energy range and the second scintillator is preferentially responsive to x-radiation having a second energy range, and wherein the first energy range is lower than the second energy range.

15. The radiation detector of claim 10 including plurality of radiation detectors disposed a multi-dimensional array.

16. The detector of claim 10 including
    a third scintillator which absorbs radiation and emits light at a third wavelength, the third wavelength being shorter than the second wavelength;
    a third photodiode which receives light emitted by the first, second, and third scintillators, wherein the third photodiode has a long wavelength cutoff which is shorter than the first and second wavelengths and longer than the third wavelength.

17. An apparatus comprising:
    a radiation source which emits radiation from a plurality of positions about an examination region;
    a plurality of detectors, each detector including:
      a radiation receiving face which faces the examination region;
      a first scintillator which preferentially absorbs radiation having a first energy and produces light at a first wavelength;
      a second scintillator which preferentially absorbs radiation having a second energy and produces light at a second wavelength;
      a first photodetector having a first long wavelength cutoff;

a second photodetector having a second long wavelength cutoff;

wherein the first photodetector is disposed between the second photodetector and the radiation receiving face, the second scintillator is disposed between the first photodetector and the radiation receiving face, the first scintillator is disposed between the second scintillator and the radiation receiving face, and the first long wavelength cutoff is shorter than the second long wavelength cutoff;

a first electrical contact; and a second electrical contact, wherein the first and second electrical contacts are in electrical communication with the first photodetector through vias disposed in the second photodetector.

18. The apparatus of claim 17 wherein the first long wavelength cutoff is shorter than the first wavelength and longer than the second wavelength.

19. The apparatus of claim 17 wherein the first and second photodetectors comprise corresponding first and second PIN photodiodes.

20. The apparatus of claim 19 wherein the first and second photodiodes are fabricated as a multi-junction device.

21. The apparatus of claim 20 further comprising a first set of electrical contacts for receiving an output signal from the first photodiode, wherein the first set of contacts is electrically connected to the first photodiode through vias extending through the second photodiode.

22. The apparatus of claim 21 wherein the first set of electrical contacts is disposed at a rear of the detector.

23. The apparatus of claim 17 wherein the first scintillator includes zinc selenide and the second scintillator includes gadolinium oxysulfide.

24. The apparatus of claim 17 wherein the radiation source includes an x-ray tube which rotates about the examination region.

* * * * *